United States Patent [19]

Diem et al.

[11] 4,242,282
[45] Dec. 30, 1980

[54] PREPARATION OF GLYOXAL

[75] Inventors: Hans Diem, Mannheim; Christian Dudeck, Limburgerhof; Gunter Lehmann, Ludwigshafen; Guenther Matthias; Norbert Petri, both of Frankenthal, all of Fed. Rep. of Germany

[73] Assignee: BASF Aktiengesellschaft, Fed. Rep. of Germany

[21] Appl. No.: 2,331

[22] Filed: Jan. 10, 1979

[30] Foreign Application Priority Data

Jan. 26, 1978 [DE] Fed. Rep. of Germany ....... 2803318

[51] Int. Cl.$^3$ .............................................. C07C 45/29
[52] U.S. Cl. ................................................... 568/471
[58] Field of Search .................................... 260/603 C

[56] References Cited

U.S. PATENT DOCUMENTS

| | | |
|---|---|---|
| 2,051,266 | 8/1936 | McAllister et al. ............. 260/603 C |
| 2,339,282 | 1/1944 | McNamee et al. .............. 260/603 C |
| 3,948,997 | 4/1976 | Howe et al. ..................... 260/603 C |
| 4,010,208 | 3/1977 | Aicher et al. ................... 260/603 C |
| 4,080,383 | 3/1978 | Deim et al. ..................... 260/603 C |

FOREIGN PATENT DOCUMENTS

| | | | |
|---|---|---|---|
| 1032732 | 11/1958 | Fed. Rep. of Germany ....... | 260/603 C |
| 1923048 | 11/1969 | Fed. Rep. of Germany ....... | 260/603 C |
| 2634439 | 2/1977 | Fed. Rep. of Germany ....... | 260/603 C |
| 836828 | 6/1960 | United Kingdom ................ | 260/603 C |
| 136352 | 1/1961 | U.S.S.R. ............................. | 260/603 C |

OTHER PUBLICATIONS

Ullmanns Encyklopadae der techn. chemie, vol. 8, pp. 250-252.
Proceed. Acad. Sci. USSR Chem. Ser., (1964), pp. 641-643.

*Primary Examiner*—Werren B. Lone
*Attorney, Agent, or Firm*—Keil & Witherspoon

[57] ABSTRACT

Glyoxal is prepared by oxidizing glycol in the presence of a silver catalyst of a defined particle size and under defined conditions of temperature, residence time and inert gas concentration.

The glyoxal obtainable by the process of the invention may be used in wrinkle-resist finishing, as an assistant for increasing the tensile strength and resilience of fibrous materials, a tanning agent, a hardener in the photographic industry, and a starting material for the manufacture of synthetic resins, textile auxiliaries, for example to prevent shrinkage after washing, paper additives, for example for increasing the wet strength, and plastics.

14 Claims, No Drawings

PREPARATION OF GLYOXAL

The present invention relates to a process for the preparation of glyoxal by oxidizing glycol in the presence of a silver catalyst of a defined particle size and under defined conditions of temperature, residence time and inert gas concentration.

Ullmanns Encyklopadie der technischen Chemie, volume 8, pages 250–252, discloses that one of the most important processes for the preparation of glyoxal is the oxidation of ethylene glycol by means of air. The conditions quoted are temperatures of 573–598° K., a copper oxide catalyst and the addition of halogen compounds. A 32 per cent strength glyoxal solution is obtained from the reaction mixture by absorption of the product in a glyoxal solution or in water. Such a process gives yields of at most 65 per cent and space-time yields of only 0.04–1.5 grams of glyoxal/cm$^3$ of catalyst volume per hour.

Proceed. Acad. Sci. USSR, Chem. Ser. (1964), 641–643 discloses the use of silver as a catalyst on pumice and alumina as the carrier. It is found that such catalysts give only poor results. For this reason, silver spirals are used as the catalyst. The best result is obtained with silver spirals at 873° K. under a pressure of 544–816 mbar, the yield being 69 per cent. The end product is obtained in the form of a 25 per cent strength aqueous solution which additionally contains 5–10 per cent of glycol. The disclosed data are found to correspond to a residence time of 0.037 second or a space-time yield of 4.46 gram of glyoxal per hour per cm$^3$ of catalyst volume. Additional inert gas is not used. Working under reduced pressure is again unsatisfactory in respect of the spacetime yield.

Russian Pat. No. 136,352 describes the oxidation of glycol at 773–973° K., using silver on aluminum oxide (40% of Ag) as the catalyst. Before use, the catalyst is heated for 2 hours at 873–973° K. The flow rate is 2.1 meters per second. The starting mixture contains 40 per cent of glycol and 60 per cent of water. The yield is 61 per cent and the space-time yield is 12.8 grams of glycol per hour per gram of catalyst. The process has the disadvantage that the preparation of the catalyst is complicated and that a rather dilute glycol solution must be employed. When the catalyst is spent, for example due to poisoning, its reprocessing entails numerous chemical operations.

German Published Application DAS No. 1,032,732 states that when using copper and silver as the catalyst a promoter, for example $TiO_2$ and $Mo_2O_5$, is required, and that inhibitors, for example HCl, $Cl_2$ or ethylene chloride, must be added in order to increase the yield. According to this publication, the best result achieved is a space-time yield of 0.043 gram per cm$^3$ per hour. This publication further teaches that the results can be improved by supporting the silver on a pumice, silica gel or aluminum oxide carrier. The process is carried out at 573–723° K. using an air-nitrogen mixture, having an oxygen content of from 1.6 to 5 per cent. The yield is 55 per cent and the space-time yield achieved is 0.104 gram of glyoxal per cm$^3$ of catalyst space per hour; this space-time yield is unsatisfactory.

German Laid-Open Application DOS No. 1,923,048 describes the preparation of glyoxal using a catalyst comprising 2 components (a and b), namely (a) copper or silver and/or gold and (b) germanium, tin, lead, nitrogen, phosphorus, arsenic, antimony and/or bismuth. The use of silver together with tin, phosphorus and/or arsenic is preferred, and overall, in particular, copper is preferred over silver. The reaction temperature is stated to be about 450–880° K., preferably about 570–720° K. Diluent gases may be used, the preferred molar ratio of the latter to oxygen being from 5:1 to 200:1. Suitable residence times are from 0.1 to 20 seconds, values from 1 to 5 seconds being preferred. The sole Example using a copper-free silver catalyst (silver/phosphorus) (in comparison, numerous Examples with copper catalysts are given) is carried out at about 700–720° K. The data correspond to an unsatisfactory space-time yield. The involved method of preparation of the catalyst is a further disadvantage.

German Laid-Open Application DOS No. 2,634,439 uses a catalyst which consists of phosphorus combined with Cu and/or Ag. A bromine compound is added in carrying out the reaction; this compound suffices to increase the yield of glyoxal but is not so great as to produce a substantial increase in the formation of glycolaldehyde or to lower the conversion of the ethylene glycol to less than about 90 per cent. An inert gas is added. In the Examples, a copper/silver/phosphorus catalyst is used in every case. The space-time yield is only 1.5 grams of glyoxal per cm$^3$ of catalyst per hour. A further disadvantage is that the catalyst can only be regenerated by involved methods.

All these processes are unsatisfactory in respect of simple and economical operation, simple preparation of the catalyst and good space-time yields.

We have found that glyoxal may be produced continuously, in an advantageous manner, by oxidizing glycol in the presence of a silver catalyst at an elevated temperature, if this oxidation is carried out in the presence of silver crystals having a particle size of from 0.1 to 2.5 millimeters and of an inert gas in a ratio of at least 4.4 moles of inert gas per mole of oxygen, with a residence time of at most 0.05 second, at from 720 to 980° K.

The reaction can be represented by the following equation:

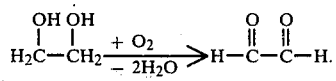

Compared to the conventional processes, the process according to the invention surprisingly gives, more simply and more economically, a better overall result in respect of yield, purity of the end product and life of the catalyst. The space-time yield is relatively better. Involved preparation and regeneration of the catalyst is avoided.

Compared to the processes described above, the catalyst of the invention has a longer life and can be obtained more simply and more economically. Silver crystals of all particle sizes, including those formed in the electrolytic production of silver granules, can be used. Accordingly, using the process according to the invention the electrolysis apparatus can be better utilized and its size can be selected accordingly; less energy, fewer operatives and less auxiliary materials, eg. nitric acid, are required, and operations such as washing, screening and drying of the silver are simplified. In the conventional processes, the silver must additionally first be applied to a carrier, or the silver must subsequently be metered. In the case of silver spirals, the latter must be produced manually. All these advantageous results of the process according to the invention are surprising. It was not to be expected from the prior art that by using pure silver crystals of a specific particle size instead of using silver spirals or silver on carriers or silver with promoters (phosphorus), an increase in the rate of reaction and hence in the space-time yield, and more particularly a substantial increase, would be possible.

Suitable starting materials for the process are pure ethylene glycol, technical-grade ethylene glycol and crude ethylene glycol and, advantageously, mixtures of these with water; the concentration of the aqueous mixtures can advantageously be from 30 to 70 percent by weight, preferably from 45 to 55 percent by weight, of ethylene glycol. Advantageously, solutions of from 49.5 to 50.5 percent strength by weight, or mixtures of the two components in equal proportions by weight, are used. The ethylene glycol is introduced into the reaction space as vapor, advantageously mixed with steam, with or without an inert gas. Advantageous gases which are inert under the reaction conditions are noble gases, eg. xenon, argon, neon and helium; alkanes, eg. methane, ethane, propane, 2,2-dimethylpropane, butane, pentane and isobutane; gaseous organic compounds of elements, e.g. tetramethylsilane; ethers, e.g. dimethyl ether and methyl ethyl ether; and, preferably, nitrogen, carbon monoxide and/or carbon dioxide; and mixtures of the above. The inert gas can be used by itself or as a mixture with steam and/or glycol vapor or, advantageously, as a mixture with air. The molar ratio of inert gas to oxygen is at least 4.4:1, suitably from 4.4:1 to 20:1, advantageously from 6:1 to 10:1. These data always relate to the total amount of inert gas, ie. including the inert gas content of the air, air being the preferred oxidant. The reaction off-gas may itself also be used as inert gas, since as a rule all it contains in addition to the inert gases nitrogen, carbon monoxide, carbon dioxide, hydrogen and steam is residual unconverted starting material, which is thus reutilized. Both pure oxygen and gases containing free oxygen, especially air, may be used as the oxidant. The oxygen, as a rule in the form of air, and the ethylene glycol are advantageously employed in a molar ratio of from 0.5 to 1.2, especially from 0.7 to 1, mole of oxygen per mole of ethylene glycol. Preferably, the total amount of steam is not more than 5, advantageously from 1 to 4, moles per mole of ethylene glycol. The air, with or without inert gas, may be introduced directly into the ethylene glycol vaporizer, advantageously into the boiling ethylene glycol/water mixture, or be introduced at any point upstream of the catalyst. The residence time in the reaction space is at most 0.05, advantageously from 0.005 to 0.04, more especially from 0.001 to 0.03, and preferably from 0.001 to 0.021, second.

The total thickness of the catalyst bed is advantageously from 15 to 50, preferably from 20 to 30, millimeters. The catalyst particles, in the form of silver crystals, are advantageously present in the catalyst bed of the reactor (which is usually vertical) in one layer or, depending on particle size, in an upper or lower part of the total bed or, depending on particle size, in an upper, middle or lower part of the total bed. The total catalyst bed advantageously rests on a silver or stainless steel net, which has been heattreated beforehand. In the case of large reactors, with diameters of more than 15 cm, the net is advantageously corrugated before being fitted into the reactor. Advantageously, the net rests on a perforated plate. It is advantageous to locate a water cooler immediately below the perforated plate. The starting mixture of ethylene glycol vapor, inert gas and oxygen or air, with or without steam, in general passes downward through the reactor, so that the upper layer or upper layers constitute the part which faces the starting mixture. In reactors of a different construction, or with different flow of the starting mixture, all statements made in the description relating to the upper (lower) part of the catalyst apply equivalently to the corresponding part facing the starting mixture (facing the reaction mixture which issues); for example, in a horizontal reactor they apply to the front (rear) part of the catalyst. If the catalyst comprises one layer only, the latter contains silver crystals having a particle size of from 0.1 to 2.5, advantageously from 0.1 to 2, preferably from 0.2 to 1, millimeter. In a 2-layer catalyst, the upper component layer advantageously contains from 20 to 60, preferably from 25 to 50, percent by weight of the catalyst, the particle sizes being from 0.1 to 0.75 millimeter, whilst the lower component layer contains from 40 to 80, preferably from 50 to 75, percent by weight of the catalyst, the particle sizes being from 0.75 to 2.5, advantageously from 0.75 to 1, millimeter.

In a 3-layer catalyst, the lower part advantageously contains from 72.5 to 89, preferably from 77.5 to 82.5, percent by weight of all catalyst particles, the middle part from 2.5 to 7.5, preferably from 4.5 to 6.5, percent by weight of all catalyst particles and the upper part from 8.5 to 20, preferably from 13 to 16, percent by weight of all catalyst particles. The particles in the lower part of the bed have sizes of from 1 to 2.5 millimeters, those in the middle part from 0.75 to 1 millimeter and those in the upper part from 0.1 to 0.75 millimeter.

Advantageously, the throughput is from 0.2 to 3 tonnes, especially from 0.3 to 1 tonne, of ethylene glycol per $m^2$ of catalyst bed cross-section per hour. In industrial operation, the catalyst bed diameter is preferably at least 0.2, advantageously 0.5 to 2, meters.

To carry out the oxidation, a gas mixture of ethylene glycol vapor, air, inert gas and, advantageously, steam, in the above amounts, is passed through the silver catalyst at 720°–980° K., preferably 770°–980° K. The process is in general carried out continuously, at pressures of from 0.8 to 2 bar, preferably from 0.8 to 1.8 bar, especially from 1.05 to 1.5 bar. It is advantageous to cool the reaction gases, leaving the catalyst zone, within a short time, for example to 270°–370° K. The cooled gas mixture is then advantageously fed to an absorption tower, in which the end product is washed out of the gas mixture by means of water or, more advantageously, by means of a 20 to 50 percent strength by weight aqueous glyoxal solution, preferably in countercurrent. In general, the aqueous solutions, advantageously in a 40 percent strength by weight form, are employed directly, but if necessary the end product can be isolated in the conventional manner, for example by azeotropic distillation with ethylbenzene and fractional distillation of the residue.

If desired, inhibitors may also be added to the starting mixture, advantageously by introduction into the vapor/gas stream of the remaining components, upstream of the catalyst. Advantageous inhibitors are halohydrocarbons, especially bromohydrocarbons and chlorohydrocarbons, eg. tetrachloroethylene, 1,1,2,2- and 1,1,1,2-tetrachloroethane, amyl chloride, cyclohexyl chloride, 1,2-dichloropropane, methylene chloride, dichlorobutane, isopropyl bromide, n-propyl bromide, butyl bromide, chloroform, bromoform, ethyl iodide, propyl iodide, chloronaphthalene, dichloronaphthalene, carbon tetrachloride, 1,1,1- and 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and isobutyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane, and corresponding mixtures. Particularly preferred inhibitors are HCl, $Cl_2$ and bromoform. The inhibitor is advantageously used in an amount of from 0.01 to 0.8 percent by weight, preferably from 0.05 to 0.5 percent by weight, based on ethylene glycol.

The glyoxal obtainable by the process of the invention may be used in wrinkle-resist finishing, as an assistant for increasing the tensile strength and resilience of fibrous materials, a tanning agent, a hardener in the photographic industry, and a valuable starting material for the manufacture of synthetic resins, textile auxiliaries, for example to prevent shrinkage after washing, paper additives, for example for increasing the wet strength, and plastics. With regard to such uses, reference may be made to the publications mentioned earlier and to Ullmann (loc. cit.).

In the Examples which follow, parts are by weight.

EXAMPLE 1

An installation comprising an ethylene glycol vaporizer and a vertical tubular reactor is employed. At its top, the reactor possesses an inlet for the vapor-form starting mixture, and the reactor cover. The catalyst bed is below the reactor top, followed, lower still, by a cooling zone. The reactor is connected to 4 absorption columns.

45 parts of a silver crystal catalyst of the following composition are introduced into the reactor:

|  | Proportion of catalyst (% by weight) | Particle size mm |
|---|---|---|
| Layer 1 | 15 | 0.1–0.75 |
| Layer 2 | 5 | 0.75–1 |
| Layer 3 | 80 | 1–2.5 |

The height of the catalyst is 30 mm. Per hour, a mixture of 246 parts of ethylene glycol, 246 parts of water and 456 parts of air is introduced into the vaporizer, and vaporized therein. After addition of 340 parts per hour of nitrogen, as the inert gas, to the vapor-form starting mixture, the latter is passed through the catalyst and reacted at 870° K. and 1.12 bar. The residence time is 0.02 second. The reaction mixture is now cooled to 320° K. and dissolved in a 27.5 percent strength by weight aqueous glyoxal solution which contains 1.2 percent of glycol. The mixture to be absorbed has the same composition, so that the concentration does not alter. During the absorption, an amount of end product corresponding to the amount freshly formed is taken off continuously. Per hour, 152 parts of glyoxal, corresponding to a yield of 66% of theory based on glycol employed, are obtained in the form of a 27.5 percent strength by weight glyoxal solution. The life of the catalyst is 90 days. The glyoxal solution contains 1.2 percent by weight of ethylene glycol and 1.6 percent by weight of formaldehyde. The conversion is 97.8 percent and the space-time yield is 14.6 g of glyoxal per $cm^3$ of catalyst volume per hour.

EXAMPLE 2

The same installation as in Example 1 is used. The reaction is carried out as described in Example 1, 0.1 part of bromoform being added per hour to the vapor-form starting mixture upstream of the catalyst.

133 parts per hour of glyoxal, corresponding to a yield of 66.4% of theory, are obtained in the form of a 33.0 percent strength by weight glyoxal solution. The life of the catalyst is 85 days. The glyoxal solution contains 0.4 percent by weight of glycol and 1.5 percent by weight of formaldehyde. The conversion is 98 percent and the space-time yield is 9.4 grams of glyoxal per $cm^3$ of catalyst volume per hour.

EXAMPLE 3

The same installation as in Example 1 is used. 45 parts of a silver crystal catalyst of the following composition are introduced into the reactor:

|  | Proportion of catalyst (% by weight) | Particle size mm |
|---|---|---|
| Layer 1 | 30 | 0.1–0.75 |
| Layer 2 | 70 | 0.75–1 |

The reaction is carried out as described in Example 1.

152 parts per hour of glyoxal, corresponding to a yield of 66% of theory, are obtained in the form of a 27.5 percent strength by weight glyoxal solution. The life of the catalyst is 80 days. The glyoxal solution contains 1.2 percent by weight of glycol and 1.4 percent by weight of formaldehyde. The conversion is 97.9 percent and the space-time yield is 14.6 grams of glyoxal per $cm^3$ of catalyst volume per hour.

We claim:

1. A process for the continuous preparation of glyoxal by oxidizing ethylene glycol in the presence of a catalyst consisting essentially of silver in crystalline form at an elevated temperature, wherein the oxidation is carried out in the presence of said crystalline silver, the crystals having particle sizes of from 0.1 to 2.5 millimeters, and of a gas inert under the reaction conditions, in a ratio of at least 4.4 moles of said inert gas per mole of oxygen, with a residence time of at most 0.05 second, at from 720° to 980° K.

2. A process as set forth in claim 1, wherein the reaction is carried out with xenon, argon, neon, helium, methane, ethane, propane, 2,2-dimethylpropane, butane, pentane, isobutane, tetramethylsilane, dimethyl ether, methyl ethyl ether, nitrogen, carbon monoxide and/or carbon dioxide as the inert gas.

3. A process as set forth in claim 1, wherein the reaction is carried out with a molar ratio of inert gas to oxygen of from 4.4:1 to 20:1.

4. A process as set forth in claim 1, wherein the reaction is carried out with a molar ratio of from 0.5 to 1.2 moles of oxygen, in the form of air, per mole of ethylene glycol, and with a total amount of steam of not more than 5 moles per mole of ethylene glycol.

5. A process as set forth in claim 1, wherein the reaction is carried out with a residence time of from 0.0005 to 0.04 second in the reaction space.

6. A process as set forth in claim 1, wherein the reaction is carried out with a residence time of from 0.001 to 0.03 second in the reaction space.

7. A process as set forth in claim 1, wherein the reaction is carried out with a total thickness of the catalyst bed of from 15 to 50 millimeters.

8. A process as set forth in claim 1, wherein the reaction is carried out with the catalyst in the form of a single layer of silver crystals having a particle size of from 0.1 to 2 millimeters.

9. A process as set forth in claim 1, wherein the reaction is carried out with a 2-layer catalyst and the upper component layer contains from 20 to 60 percent by weight of the catalyst, the particle sizes being from 0.1 to 0.75 millimeter, whilst the lower component layer contains from 40 to 80 percent by weight of the catalyst, the particle sizes being from 0.75 to 2.5 millimeter.

10. A process as set forth in claim 1, wherein the reaction is carried out with a 3-layer catalyst and the lower part contains from 72.5 to 89 percent by weight of all catalyst particles, the middle part from 2.5 to 7.5 percent by weight of all catalyst particles and the upper part from 8.5 to 20 percent by weight of all catalyst particles and the particles in the lower part of the bed have sizes of from 1 to 2.5 millimeters, those in the middle part from 0.75 to 1 millimeter and those in the upper part from 0.1 to 0.75 millimeter.

11. A process as set forth in claim 1, wherein the reaction is carried out at from 770° to 980° K.

12. A process as claimed in claim 1, wherein the reaction is carried out at pressures of from 0.8 to 2 bar.

13. A process as set forth in claim 1, wherein the reaction is carried out with tetrachloroethylene, 1,1,2,2- or 1,1,1,2-tetrachloroethane, amyl chloride, cyclohexyl chloride, 1,2-dichloropropane, methylene chloride, dichlorobutane, isopropyl bromide, n-propyl bromide, butyl bromide, chloroform, bromoform, ethyl iodide, propyl iodide, chloronaphthalene, dichloronaphthalene, carbon tetrachloride, 1,1,1- or 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- or iso-butyl chloride, chlorobenzene, fluorobenzene, bromobenzene, iodobenzene, o-, p- or m-dichlorobenzene, o-, p- or m-dibromobenzene, o-, m- or p-chlorotoluene, 1,2,4-trichlorobenzene, 1,10-dibromodecane, 1,4-dibromobutane, HCl or $Cl_2$ as the inhibitor.

14. A process as set forth in claim 1, wherein the reaction is carried out with from 0.01 to 0.8 percent by weight, based on ethylene glycol, of an inhibitor.

* * * * *